US010646546B2

(12) United States Patent
Im et al.

(10) Patent No.: US 10,646,546 B2
(45) Date of Patent: May 12, 2020

(54) AFLIBERCEPT OPHTHALMIC PHARMACEUTICAL COMPOSITION

(71) Applicant: SAM CHUN DANG PHARM. CO., LTD., Hwaseong-si, Gyeonggi-do (KR)

(72) Inventors: Guang-Jin Im, Ansan-si (KR); Byung-Jhip Ha, Icheon-si (KR); Na-Won Park, Suwon-si (KR); Yong-Seop Park, Suwon-si (KR)

(73) Assignee: SAM CHUN DANG PHARM. CO., LTD., Hwasseong-si, Gyeonggi-do (KR)

( * ) Notice: Subject to any disclaimer, the term of this patent is extended or adjusted under 35 U.S.C. 154(b) by 0 days.

(21) Appl. No.: 16/305,987

(22) PCT Filed: Oct. 13, 2017

(86) PCT No.: PCT/KR2017/011293
§ 371 (c)(1),
(2) Date: Nov. 30, 2018

(87) PCT Pub. No.: WO2018/199408
PCT Pub. Date: Nov. 1, 2018

(65) Prior Publication Data
US 2019/0160145 A1 May 30, 2019

(30) Foreign Application Priority Data

Apr. 26, 2017 (KR) .................. 10-2017-0053782
Sep. 19, 2017 (KR) .................. 10-2017-0120262

(51) Int. Cl.
*A61K 38/17* (2006.01)
*A61K 9/00* (2006.01)
*A61K 47/12* (2006.01)
*A61K 47/26* (2006.01)

(52) U.S. Cl.
CPC .......... *A61K 38/179* (2013.01); *A61K 9/0048* (2013.01); *A61K 47/12* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 7,608,261 B2 | 10/2009 | Furfine et al. |
| 7,807,164 B2 | 10/2010 | Furfine et al. |
| 8,092,803 B2 | 1/2012 | Furfine et al. |
| 8,481,046 B2 | 7/2013 | Furfine et al. |
| 8,802,107 B2 | 8/2014 | Furfine et al. |
| 9,198,859 B2 | 12/2015 | Keller et al. |
| 9,340,594 B2 | 5/2016 | Furfine et al. |
| 9,580,489 B2 | 2/2017 | Furfine et al. |
| 2007/0293432 A1 | 12/2007 | Furfine et al. |
| 2010/0075903 A1 | 3/2010 | Furfine et al. |
| 2011/0257601 A1 | 10/2011 | Furfine et al. |
| 2012/0087929 A1 | 4/2012 | Furfine et al. |
| 2012/0118991 A1 | 5/2012 | Keller et al. |
| 2013/0274189 A1 | 10/2013 | Furfine et al. |
| 2013/0323242 A1 | 12/2013 | Everett et al. |
| 2014/0323983 A1 | 10/2014 | Furfine et al. |
| 2015/0157709 A1 | 6/2015 | Everett et al. |
| 2015/0182623 A1 | 7/2015 | Everett et al. |
| 2016/0213608 A1 | 7/2016 | Furfine et al. |
| 2016/0213789 A1 | 7/2016 | Rim et al. |
| 2016/0244505 A1 | 8/2016 | Furfine et al. |
| 2016/0376342 A1 | 12/2016 | Park et al. |

FOREIGN PATENT DOCUMENTS

| | | |
|---|---|---|
| EP | 2 248 517 A1 | 11/2010 |
| KR | 10-2009-0018807 A | 2/2009 |
| KR | 10-2015-0033620 A | 4/2015 |
| KR | 10-2015-0035681 A | 4/2015 |
| KR | 10-2017-0000356 A | 1/2017 |

OTHER PUBLICATIONS

Aiello et al., "Vascular Endothelial Growth Factor in Ocular Fluid of Patients with Diabetic Retinopathy and Other Retinal Disorders", The New England Journal of Medicine, vol. 331, pp. 1480-1487, (1994).
Amin et al., "Growth Factor Localization in Choroidal Neovascular Membranes of Age-Related Macular Degeneration", Invest Ophthalmol Vis Sci., vol. 35, pp. 3178-3188, (1994).

*Primary Examiner* — Elly-Gerald Stoica
(74) *Attorney, Agent, or Firm* — Vorys, Sater, Seymour and Pease LLP; Mih Suhn Koh

(57) ABSTRACT

Provided is an ophthalmic pharmaceutical composition having a certain pH, comprising aflibercept as an active ingredient and an acetate salt buffering agent, wherein the composition is free of an ionic tonicity agent, remarkably reduces the formation of dimeric and multimeric impurities, and maintains the biological activity in a high level for a long time, under the accelerated and stress conditions as well as under the cold storage condition.

12 Claims, 1 Drawing Sheet

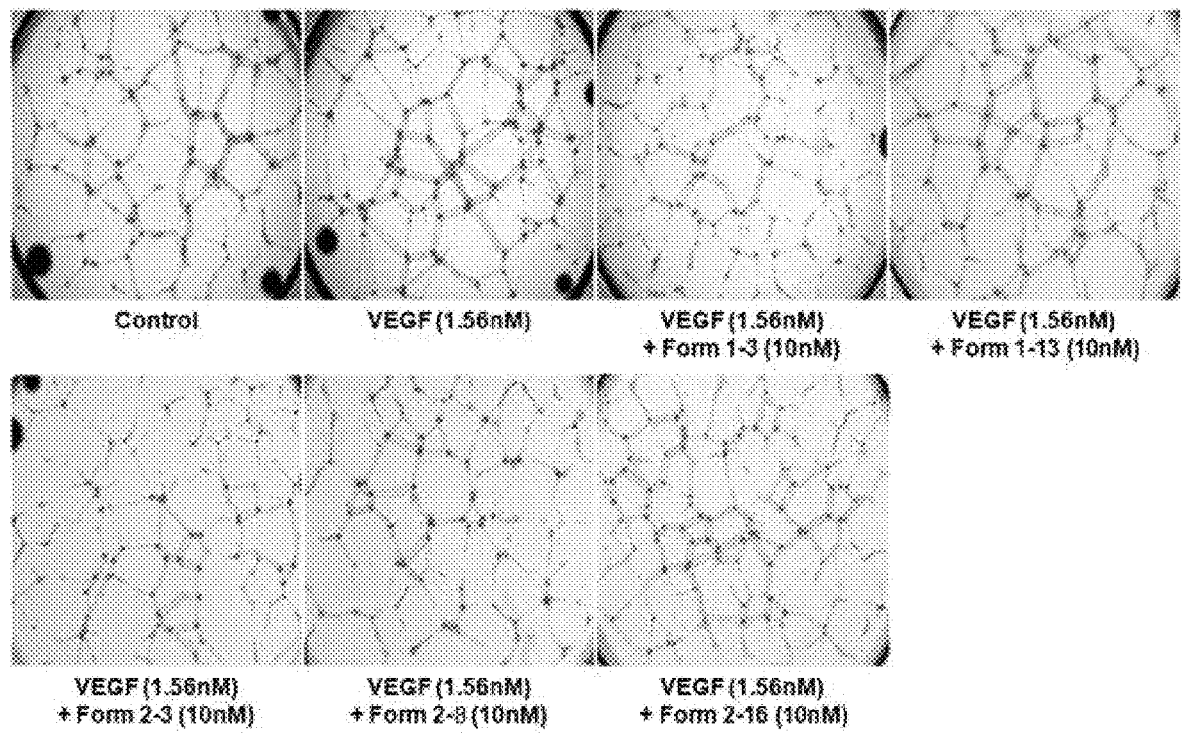

AFLIBERCEPT OPHTHALMIC PHARMACEUTICAL COMPOSITION

TECHNICAL FIELD

The present invention relates to an ophthalmic pharmaceutical composition comprising aflibercept as an active ingredient. More specifically, the present invention relates to an aflibercept-containing ophthalmic pharmaceutical composition having a certain pH, which comprises an acetate salt buffering agent and is free of an ionic tonicity agent.

BACKGROUND ART

Angiogenesis is known to involve in the pathogenesis of various diseases such as solid tumors, proliferative retinopathies, age-related macular degeneration (AMD), and rheumatoid arthritis. Vascular endothelial growth factor (VEGF), one of the factors necessary for angiogenesis, is expressed in human cancers and plays an important role in tumor neoangiogenesis. In addition, the presence of VEGF in a high concentration in the eye fluid is highly correlated with the vascularization activity in diabetic and other ischemic retinopathy patients (Aiello L P, et al., N Engl J Med 1994; 331: 1480-1487) and leads to localization of growth factors in the choroidal neovascular membranes of age-related macular degeneration (AMD) patients (Amin R1, et al. Invest Ophthalmol Vis Sci. 1994 Jul.; 35(8): 3178-88). Therefore, anti-VEGF antibodies or VEGF inhibitors may be promising candidates for the treatment of solid tumor and diseases associated with angiogenesis in the eye.

Aflibercept, one of the VEGF inhibitors, is a recombinant fusion protein consisting of VEGF-binding portions from the extracellular domains of human VEGF receptors 1 and 2 that are fused to the Fc portion of the human IgG1 immunoglobulin. Aflibercept has been approved in the United States and Europe for the treatment of wet macular degeneration under the trade name Eylea™.

Physicochemical modifications occur in protein-containing pharmaceutical compositions under the non-optimal condition. In particular, factors such as concentration of a protein, type of buffering agents, type and concentration of stabilizing agents, type and concentration of organic co-solvents, concentration of a salt, pH, temperature, and contact with air, significantly affect oxidation, deamidation, isomerization, and polymerization of a protein. These modifications cause aggregations, fragments, isomers of the protein, so that the biological activity thereof may be reduced. Especially, protein aggregation, which is a major internal factor in the formation of insoluble microparticles, may cause side effects such as immune reactions. And also, because of the characteristics of ophthalmic formulations, the insoluble particles should be strictly restricted or controlled.

Korean Patent No. 10-1406811 (International Patent Publication No. WO 2007/149334) has disclosed an ophthalmic formulation and a lyophilizable formulation having pH 5.8 to 7.0, which comprises aflibercept; an organic co-solvent such as polysorbate; an ionic tonicity agent selected from sodium chloride or potassium chloride; a sodium phosphate buffering agent; and a stabilizer such as sucrose, each being in a specific concentration. The formulation disclosed in Korean Patent No. 10-1406811 may be applied to a prefilled syringe suitable for intravitreal administration.

It has been described that the ophthalmic formulation and lyophilizable formulation disclosed in Korean Patent No. 10-1406811 have an effect of inhibiting production of impurities and byproducts due to aggregation, fragmentation and isomerization of aflibercept. However, said formulations were problematic in that the effect of stabilizing aflibercept was markedly reduced under the stress condition, e.g., under high temperature condition of 40° C. or more (Korean Patent Publication No. 10-2017-0000356).

DISCLOSURE

Technical Problem

The present inventors carried out various researches in order to develop a stable ophthalmic preparation which can minimize the formation of aflibercept-derived impurities (dimeric or multimeric impurities) under the accelerated and stress conditions, as well as under the cold storage condition. Especially, the present inventors carried out various formulation studies including buffering agents, isotonic agents, pH ranges, and the like. As the result thereof, the present inventors have found that the use of an ionic tonicity agent such as NaCl causes the formation of dimeric or multimeric impurities derived from aflibercept. And also, the present inventors have found that, when the tonicity is adjusted by controlling the amount of sugar or sugar alcohol without using an ionic tonicity agent such as NaCl; and the pH is adjusted to pH 5.2 to 5.7 by using a specific buffering agent (an acetate salt buffering agent), the formation of dimeric and multimeric impurities can be remarkably reduced and; the biological activity can be maintained at a high level for a long time.

Therefore, the present invention provides an aflibercept-containing ophthalmic pharmaceutical composition having pH 5.2 to 5.7, which comprises an acetate salt buffering agent and is free of an ionic tonicity agent.

Technical Solution

In accordance with an aspect of the present invention, there is provided an ophthalmic pharmaceutical composition having a pH ranging from pH 5.2 to 5.7, comprising (a) a therapeutically effective amount of aflibercept; (b) an acetate salt buffering agent 5 to 50 mM; (c) a sugar 6 to 12 w/v % or a sugar alcohol 3 to 7 w/v %; and (d) a surfactant 0.01 to 0.1 w/v % in an aqueous medium, wherein the ophthalmic pharmaceutical composition is free of an ionic tonicity agent.

The aflibercept may be present in a concentration ranging from 20 to 50 mg/ml.

The acetate salt buffering agent may be a sodium acetate buffering agent. The acetate salt buffering agent may be present in a concentration ranging preferably from about 10 to 20 mM, more preferably about 10 to 15 mM.

The sugar may be preferably sucrose, trehalose, or a mixture thereof, more preferably sucrose or trehalose, most preferably sucrose. The sugar may be present in a concentration ranging from about 6 to 8 w/v %. And also, the sugar alcohol may be sorbitol. The sugar alcohol may be present in a concentration of about 5 w/v %.

The surfactant may be polyoxyethylene sorbitan fatty acid ester, polyoxyethylene-polyoxypropylene block copolymer, or a mixture thereof, preferably polyoxyethylene (20) sorbitan monolaurate or polyoxyethylene (20) sorbitan monooleate, more preferably polyoxyethylene (20) sorbitan monolaurate. In an embodiment, the surfactant may be present in a concentration of about 0.03 w/v %.

In an embodiment of the present invention, there is provided an ophthalmic pharmaceutical composition having about pH 5.5, consisting of aflibercept 40 mg/ml; a sodium acetate buffering agent 10 to 15 mM; sucrose 7 w/v %; polyoxyethylene (20) sorbitan monolaurate 0.03 w/v %, and an aqueous medium.

In another embodiment of the present invention, there is provided an ophthalmic pharmaceutical composition having about pH 5.5, consisting of aflibercept 40 mg/ml; a sodium acetate buffering agent 10 to 15 mM; trehalose 8 w/v %; polyoxyethylene (20) sorbitan monolaurate 0.03 w/v %, and an aqueous medium.

Advantageous Effects

It has been found by the present invention that the use of an ionic tonicity agent such as NaCl not only causes the formation of dimeric or multimeric impurities derived from aflibercept but also affects the biological activity thereof. In the ophthalmic pharmaceutical composition according to the present invention, the tonicity is adjusted by controlling the amount of sugar or sugar alcohol without using an ionic tonicity agent such as NaCl; and the pH is adjusted to pH 5.2 to 5.7 by using an acetate salt buffering agent, thereby being able to reduce the formation of dimeric and multimeric impurities under the accelerated and stress conditions as well as under the cold storage condition; and maintain the biological activity at a high level for a long time. Therefore, the ophthalmic pharmaceutical composition according to the present invention improves the physicochemical and biological stabilities, thereby being able to be suitably applied to a prefilled syringe for intravitreal administration and intraocular administration in patients suffering from various ophthalmic diseases such as wet age-related macular degeneration and diabetic macular edema.

DESCRIPTION OF DRAWINGS

The FIGURE shows the results obtained by performing the tube formation assay of human umbilical vein endothelial cells (HUVECs) using the ophthalmic pharmaceutical composition of the present invention.

BEST MODE

The present invention provides an ophthalmic pharmaceutical composition having a pH ranging from pH 5.2 to 5.7, comprising (a) a therapeutically effective amount of aflibercept; (b) an acetate salt buffering agent 5 to 50 mM; (c) a sugar 6 to 12 w/v % or a sugar alcohol 3 to 7 w/v %; and (d) a surfactant 0.01 to 0.1 w/v % in an aqueous medium, wherein the ophthalmic pharmaceutical composition is free of an ionic tonicity agent.

The aflibercept used as an active ingredient in the pharmaceutical composition of the present invention may be included in a therapeutically effective amount. For example, aflibercept may be present in a concentration ranging from 10 to 50 mg/ml, preferably in a concentration ranging from 20 to 50 mg/ml, more preferably in a concentration of about 40 mg/ml, but not limited thereto.

The aqueous medium includes any aqueous medium which is able to provide a buffer along with an acetate salt buffering agent. For example, the aqueous medium includes water for injection, sterile distilled water, and so on.

The acetate salt buffering agent includes alkali metal acetates or alkaline earth metal acetates. For example, the acetate salt buffering agent may be a sodium acetate buffering agent. A desired pH may be provided by controlling the ratio between acetate and the metal (e.g., sodium) in the buffering agent. The acetate salt buffering agent may be present in a concentration ranging from 5 to 50 mM, preferably from 5 to 30 mM, more preferably about 10 to 20 mM, most preferably about 10 to 15 mM, but not limited thereto.

The sugar may be preferably sucrose, trehalose, or a mixture thereof, more preferably sucrose or trehalose, most preferably sucrose. The sugar may be present in a concentration ranging from 6 to 12 w/v %, preferably from 6 to 10 w/v %. And also, it has been found by the present invention that, when the sugar is present in a concentration ranging from about 6 to 8 w/v %, the pharmaceutical composition shows similar osmolality to the osmolality of physiological saline (about 290 mOsmol/kg) as well as excellent stability. Therefore, most preferably, the sugar may be present in a concentration ranging from about 6 to 8 w/v %. In addition, the sugar alcohol may be sorbitol. The sugar alcohol may be present in a concentration of about 5 w/v %.

The surfactant may be polyoxyethylene sorbitan fatty acid ester (e.g., Polysorbate 20, Polysorbate 80, and so on), polyoxyethylene-polyoxypropylene block copolymer (e.g., Poloxamer 188™ and so on), or a mixture thereof, preferably polyoxyethylene (20) sorbitan monolaurate (Polysorbate 20) or polyoxyethylene (20) sorbitan monooleate (Polysorbate 80), more preferably polyoxyethylene (20) sorbitan monolaurate. The surfactant is present in a concentration ranging from 0.01 to 0.1 w/v %. In an embodiment, the polyoxyethylene sorbitan fatty acid ester may be present preferably in a concentration ranging from 0.01 to 0.03 w/v %, more preferably in a concentration of about 0.03 w/v %. In another embodiment, the polyoxyethylene-polyoxypropylene block copolymer may be present preferably in a concentration ranging from 0.03 to 0.1 w/v %.

In an embodiment of the present invention, there is provided an ophthalmic pharmaceutical composition having about pH 5.5, consisting of aflibercept 40 mg/ml; a sodium acetate buffering agent 10 to 15 mM; sucrose 7 w/v %; polyoxyethylene (20) sorbitan monolaurate 0.03 w/v %, and an aqueous medium.

In another embodiment of the present invention, there is provided an ophthalmic pharmaceutical composition having about pH 5.5, consisting of aflibercept 40 mg/ml; a sodium acetate buffering agent 10 to 15 mM; trehalose 8 w/v %; polyoxyethylene (20) sorbitan monolaurate 0.03 w/v %, and an aqueous medium.

The pharmaceutical composition of the present invention may be filled into a glass vial. In addition, the pharmaceutical composition of the present invention may be provided in the form of a prefilled syringe.

The present invention will be described in further detail with reference to the following examples. These examples are for illustrative purposes only and are not intended to limit the scope of the present invention.

Example: Preparation and Evaluation of Ophthalmic Compositions (1) Preparation of Ophthalmic Compositions Ophthalmic compositions were prepared according to the components and amounts shown in Tables 1 and 2. Each pH of the compositions was controlled by changing the ratio between sodium and acetate in the sodium acetate buffering agent or by changing the ratio between sodium and citrate in the sodium citrate buffering agent. Specifically, after preparing the sodium acetate buffer or the sodium citrate buffer having each pH, aflibercept, sugar (sucrose or trehalose) or sugar alcohol (sorbitol), and Polysorbate 20 were dissolved therein under stirring to prepare each formulation. Formulation 1-13 was prepared by using sodium phosphate as a buffering agent and additionally dissolving sodium chloride as an ionic tonicity agent. And also, Formulations 1-14, 2-13, and 2-14 were prepared by additionally dissolving sodium chloride as an ionic tonicity agent. The osmolality of each resulting formulation is shown in Tables 1 and 2.

TABLE 1

| | Active ingredient | pH | Buffering agent | Sugar/Sugar alcohol | Surfactant | Ionic tonicity agent | Osmolality (mOsm/kg) |
|---|---|---|---|---|---|---|---|
| 1-1 | Aflibercept (40 mg/ml) | 5.0 | Sodium acetate (10 mM) | Sucrose (10 w/v %) | Polysorbate 20 (0.03 w/v %) | — | 360 |
| 1-2 | Aflibercept (40 mg/ml) | 5.2 | Sodium acetate (10 mM) | Sucrose (10 w/v %) | Polysorbate 20 (0.03 w/v %) | — | 362 |
| 1-3 | Aflibercept (40 mg/ml) | 5.5 | Sodium acetate (10 mM) | Sucrose (10 w/v %) | Polysorbate 20 (0.03 w/v %) | — | 363 |
| 1-4 | Aflibercept (40 mg/ml) | 5.7 | Sodium acetate (10 mM) | Sucrose (10 w/v %) | Polysorbate 20 (0.03 w/v %) | — | 372 |
| 1-5 | Aflibercept (40 mg/ml) | 6.0 | Sodium acetate (10 mM) | Sucrose (10 w/v %) | Polysorbate 20 (0.03 w/v %) | — | 368 |
| 1-6 | Aflibercept (40 mg/ml) | 6.2 | Sodium acetate (10 mM) | Sucrose (10 w/v %) | Polysorbate 20 (0.03 w/v %) | — | 369 |
| 1-7 | Aflibercept (40 mg/ml) | 5.0 | Sodium acetate (10 mM) | Trehalose (10 w/v %) | Polysorbate 20 (0.03 w/v %) | — | 331 |
| 1-8 | Aflibercept (40 mg/ml) | 5.2 | Sodium acetate (10 mM) | Trehalose (10 w/v %) | Polysorbate 20 (0.03 w/v %) | — | 332 |
| 1-9 | Aflibercept (40 mg/ml) | 5.5 | Sodium acetate (10 mM) | Trehalose (10 w/v %) | Polysorbate 20 (0.03 w/v %) | — | 334 |
| 1-10 | Aflibercept (40 mg/ml) | 5.7 | Sodium acetate (10 mM) | Trehalose (10 w/v %) | Polysorbate 20 (0.03 w/v %) | — | 337 |
| 1-11 | Aflibercept (40 mg/ml) | 6.0 | Sodium acetate (10 mM) | Trehalose (10 w/v %) | Polysorbate 20 (0.03 w/v %) | — | 316 |
| 1-12 | Aflibercept (40 mg/ml) | 6.2 | Sodium acetate (10 mM) | Trehalose (10 w/v %) | Polysorbate 20 (0.03 w/v %) | — | 328 |
| 1-13 | Aflibercept (40 mg/ml) | 6.2 | Sodium phosphate (10 mM) | Sucrose (5 w/v %) | Polysorbate 20 (0.03 w/v %) | NaCl (40 mM) | 280 |
| 1-14 | Aflibercept (40 mg/ml) | 5.5 | Sodium acetate (10 mM) | Sucrose (5 w/v %) | Polysorbate 20 (0.03 w/v %) | NaCl (40 mM) | 266 |
| 1-15 | Aflibercept (40 mg/ml) | 5.5 | Sodium acetate (10 mM) | Sorbitol (5 w/v %) | Polysorbate 20 (0.03 w/v %) | — | 317 |

TABLE 2

| | Active ingredient | pH | Buffering agent | Sugar/Sugar alcohol | Surfactant | Ionic tonicity agent | Osmolality (mOsm/kg) |
|---|---|---|---|---|---|---|---|
| 2-1 | Aflibercept (40 mg/ml) | 5.2 | Sodium acetate (15 mM) | Sucrose (7 w/v %) | Polysorbate 20 (0.03 w/v %) | — | 273 |
| 2-2 | Aflibercept (40 mg/ml) | 5.5 | Sodium acetate (10 mM) | Sucrose (7 w/v %) | Polysorbate 20 (0.03 w/v %) | — | 266 |
| 2-3 | Aflibercept | 5.5 | Sodium | Sucrose | Polysorbate 20 | — | 272 |

TABLE 2-continued

| | Active ingredient | Buffering pH agent | Sugar/Sugar alcohol | Surfactant | Ionic tonicity agent | Osmolality (mOsm/kg) |
|---|---|---|---|---|---|---|
| | (40 mg/ml) | acetate (15 mM) | (7 w/v %) | (0.03 w/v %) | | |
| 2-4 | Aflibercept (40 mg/ml) | 5.5 Sodium acetate (20 mM) | Sucrose (6 w/v %) | Polysorbate 20 (0.03 w/v %) | — | 252 |
| 2-5 | Aflibercept (40 mg/ml) | 5.7 Sodium acetate (15 mM) | Sucrose (7 w/v %) | Polysorbate 20 (0.03 w/v %) | — | 274 |
| 2-6 | Aflibercept (40 mg/ml) | 5.2 Sodium acetate (15 mM) | Trehalose (8 w/v %) | Polysorbate 20 (0.03 w/v %) | — | 272 |
| 2-7 | Aflibercept (40 mg/ml) | 5.5 Sodium acetate (10 mM) | Trehalose (8 w/v %) | Polysorbate 20 (0.03 w/v %) | — | 265 |
| 2-8 | Aflibercept (40 mg/ml) | 5.5 Sodium acetate (15 mM) | Trehalose (8 w/v %) | Polysorbate 20 (0.03 w/v %) | — | 273 |
| 2-9 | Aflibercept (40 mg/ml) | 5.5 Sodium acetate (20 mM) | Trehalose (7 w/v %) | Polysorbate 20 (0.03 w/v %) | — | 251 |
| 2-10 | Aflibercept (40 mg/ml) | 5.7 Sodium acetate (15 mM) | Trehalose (8 w/v %) | Polysorbate 20 (0.03 w/v %) | — | 273 |
| 2-11 | Aflibercept (40 mg/ml) | 5.5 Sodium citrate (15 mM) | Sucrose (7 w/v %) | Polysorbate 20 (0.03 w/v %) | — | 277 |
| 2-12 | Aflibercept (40 mg/ml) | 5.5 Sodium citrate (15 mM) | Trehalose (8 w/v %) | Polysorbate 20 (0.03 w/v %) | — | 276 |
| 2-13 | Aflibercept (40 mg/ml) | 5.5 Sodium acetate (15 mM) | Sucrose (5 w/v %) | Polysorbate 20 (0.03 w/v %) | NaCl (40 mM) | 275 |
| 2-14 | Aflibercept (40 mg/ml) | 5.5 Sodium acetate (15 mM) | Trehalose (6 w/v %) | Polysorbate 20 (0.03 w/v %) | NaCl (40 mM) | 272 |

(2) Evaluation on the Formation of Fragments, Dimers, and Multimers Derived from Aflibercept Under the Stress and Accelerated Conditions After the storage of each formulation prepared in the above in a 3 ml glass vial at 25° C. or 40° C. for 8 weeks, the contents of aflibercept (monomer) and its fragments, dimers or multimers were measured through Size Exclusion HPLC (SEC-HPLC) and Dynamic Light Scattering (DLS) analyses. The conditions for SEC-HPLC analysis are as follows; Column: TSK-GEL G3000SWXL, 7.8×30 (ID mm×L cm) (Tosoh, Cat. #08541), Mobile phase: 200 mM potassium phosphate buffer (pH 6.2) containing 250 mM KCl and 0.05% $NaN_3$, Flow rate: 0.5 ml/min, and Wave length: 280 nm. The DLS analysis was performed by specifying the Z-Average and PDI (polydispersity Index) with the Zetasizer Nano system (Malvern).

The SEC-HPLC analysis results are shown in Tables 3 and 4; and the DLS analysis results are shown in Tables 5 and 6.

TABLE 3

Results of SEC-HPLC Analysis (stored at 25° C. for 8 weeks)

| Formulation | Aflibercept (monomer) | Fragments | Dimers | Multimers |
|---|---|---|---|---|
| 1-1 | 89.8 | N.D* | 9.1 | 1.1 |
| 1-2 | 94.2 | N.D* | 5.1 | 0.7 |
| 1-3 | 95.7 | N.D* | 3.0 | 0.3 |
| 1-4 | 95.1 | N.D* | 4.5 | 0.4 |
| 1-5 | 91.0 | N.D* | 8.1 | 0.9 |
| 1-6 | 88.3 | N.D* | 10.3 | 1.4 |
| 1-7 | 89.8 | N.D* | 9.1 | 1.1 |
| 1-8 | 93.5 | N.D* | 5.8 | 0.7 |
| 1-9 | 94.8 | N.D* | 5.1 | 0.1 |
| 1-10 | 92.7 | N.D* | 6.5 | 0.8 |
| 1-11 | 91.6 | N.D* | 7.8 | 0.6 |
| 1-12 | 86.2 | N.D* | 12.3 | 1.5 |
| 1-13 | 89.4 | N.D* | 8.9 | 1.7 |
| 1-14 | 89.1 | N.D* | 9.3 | 1.6 |
| 1-15 | 94.1 | N.D* | 5.4 | 0.5 |
| 2-1 | 93.1 | N.D* | 6.2 | 0.7 |
| 2-2 | 95.3 | N.D* | 4.1 | 0.6 |
| 2-3 | 96.2 | N.D* | 3.6 | 0.2 |
| 2-4 | 95.8 | N.D* | 3.9 | 0.3 |
| 2-5 | 94.8 | N.D* | 4.6 | 0.6 |
| 2-6 | 92.9 | N.D* | 7.1 | 0.9 |
| 2-7 | 93.8 | N.D* | 5.7 | 0.5 |
| 2-8 | 94.5 | N.D* | 5.4 | 0.4 |
| 2-9 | 94.1 | N.D* | 5.7 | 0.2 |
| 2-10 | 92.4 | N.D* | 6.8 | 0.8 |
| 2-11 | 88.5 | N.D* | 10.1 | 1.4 |
| 2-12 | 86.2 | N.D* | 11.6 | 2.2 |
| 2-13 | 88.7 | N.D* | 9.8 | 1.5 |
| 2-14 | 87.9 | N.D* | 9.6 | 2.5 |

*N.D.: not detected

TABLE 4

Results of SEC-HPLC Analysis (stored at 40° C. for 8 weeks)

| Formulation | Aflibercept (monomer) | Fragments | Dimers | Multimers |
|---|---|---|---|---|
| 1-1 | 77.1 | N.D* | 17.3 | 5.6 |
| 1-2 | 86.8 | N.D* | 10.1 | 3.1 |
| 1-3 | 90.1 | N.D* | 8.3 | 1.6 |
| 1-4 | 88.3 | N.D* | 9.1 | 2.6 |
| 1-5 | 82.7 | N.D* | 12.5 | 4.8 |
| 1-6 | 72.1 | N.D* | 18.7 | 9.2 |
| 1-7 | 75.3 | N.D* | 18.2 | 6.5 |
| 1-8 | 82.4 | N.D* | 12.4 | 5.2 |
| 1-9 | 88.5 | N.D* | 8.9 | 2.6 |
| 1-10 | 86.1 | N.D* | 11.1 | 2.8 |
| 1-11 | 78.9 | N.D* | 15.8 | 5.3 |
| 1-12 | 71.3 | N.D* | 19.1 | 9.6 |
| 1-13 | 72.9 | N.D* | 19.7 | 7.4 |
| 1-14 | 73.5 | N.D* | 19.2 | 7.3 |
| 1-15 | 90.3 | N.D* | 8.2 | 1.5 |
| 2-1 | 87.1 | N.D* | 10.2 | 2.7 |
| 2-2 | 90.5 | N.D* | 7.9 | 1.6 |
| 2-3 | 91.2 | N.D* | 7.6 | 1.2 |
| 2-4 | 91.0 | N.D* | 7.5 | 1.5 |
| 2-5 | 88.6 | N.D* | 9.2 | 2.2 |
| 2-6 | 83.3 | N.D* | 12.3 | 4.4 |
| 2-7 | 88.4 | N.D* | 9.1 | 2.5 |
| 2-8 | 89.6 | N.D* | 8.8 | 1.6 |
| 2-9 | 89.1 | N.D* | 8.9 | 2.0 |
| 2-10 | 85.0 | N.D* | 11.8 | 3.2 |
| 2-11 | 72.6 | N.D* | 17.4 | 10.0 |
| 2-12 | 67.9 | N.D* | 18.2 | 13.9 |
| 2-13 | 72.8 | N.D* | 19.2 | 8.0 |
| 2-14 | 71.2 | N.D* | 19.6 | 9.2 |

*N.D.: not detected

TABLE 5

Results of DLS Analysis (stored at 25° C. for 8 weeks)

| Formulation | Z-Average (d·nm) | PDI | Peak Mean size(d·nm) | Peak Intensity (100%) | Peak Mass (100%) |
|---|---|---|---|---|---|
| 1-1 | 14.89 | 0.083 | 15.54 | 100 | 100 |
| 1-2 | 10.12 | 0.059 | 10.10 | 100 | 100 |
| 1-3 | 10.05 | 0.054 | 10.10 | 100 | 100 |
| 1-4 | 11.24 | 0.065 | 11.70 | 100 | 100 |
| 1-5 | 13.17 | 0.078 | 13.54 | 100 | 100 |
| 1-6 | 15.42 | 0.087 | 15.69 | 100 | 100 |
| 1-7 | 15.09 | 0.088 | 15.69 | 100 | 100 |
| 1-8 | 11.84 | 0.068 | 11.70 | 100 | 100 |
| 1-9 | 10.85 | 0.061 | 10.10 | 100 | 100 |
| 1-10 | 12.22 | 0.072 | 11.70 | 100 | 100 |
| 1-11 | 13.28 | 0.079 | 13.54 | 100 | 100 |
| 1-12 | 16.36 | 0.095 | 15.69 | 100 | 100 |
| 1-13 | 15.33 | 0.089 | 15.69 | 100 | 100 |
| 1-14 | 15.14 | 0.089 | 15.69 | 100 | 100 |
| 1-15 | 10.63 | 0.060 | 10.10 | 100 | 100 |
| 2-1 | 10.56 | 0.060 | 10.10 | 100 | 100 |
| 2-2 | 10.10 | 0.055 | 10.10 | 100 | 100 |
| 2-3 | 10.02 | 0.054 | 10.10 | 100 | 100 |
| 2-4 | 10.04 | 0.054 | 10.10 | 100 | 100 |
| 2-5 | 11.18 | 0.063 | 11.70 | 100 | 100 |
| 2-6 | 11.98 | 0.070 | 11.70 | 100 | 100 |
| 2-7 | 11.10 | 0.063 | 11.70 | 100 | 100 |
| 2-8 | 11.02 | 0.062 | 11.70 | 100 | 100 |
| 2-9 | 11.04 | 0.062 | 11.70 | 100 | 100 |
| 2-10 | 12.18 | 0.072 | 11.70 | 100 | 100 |
| 2-11 | 16.11 | 0.092 | 15.69 | 100 | 100 |
| 2-12 | 16.25 | 0.094 | 15.69 | 100 | 100 |
| 2-13 | 15.46 | 0.089 | 15.69 | 100 | 100 |
| 2-14 | 15.55 | 0.090 | 15.69 | 100 | 100 |

TABLE 6

Results of DLS Analysis (stored at 40° C. for 8 weeks)

| Formulation | Z-Average (d·nm) | PDI | Peak Mean size(d·nm) | Peak Intensity (100%) | Peak Mass (100%) |
|---|---|---|---|---|---|
| 1-1 | 17.88 | 0.181 | 18.17 | 100 | 100 |
| 1-2 | 15.78 | 0.128 | 15.69 | 100 | 100 |
| 1-3 | 15.12 | 0.121 | 15.69 | 100 | 100 |
| 1-4 | 15.66 | 0.126 | 15.69 | 100 | 100 |
| 1-5 | 16.54 | 0.171 | 15.69 | 100 | 100 |
| 1-6 | 18.65 | 0.188 | 18.17 | 100 | 100 |
| 1-7 | 17.91 | 0.182 | 18.17 | 100 | 100 |
| 1-8 | 16.61 | 0.174 | 15.69 | 100 | 100 |
| 1-9 | 15.22 | 0.123 | 15.69 | 100 | 100 |
| 1-10 | 15.88 | 0.132 | 15.69 | 100 | 100 |
| 1-11 | 17.23 | 0.179 | 18.17 | 100 | 100 |
| 1-12 | 18.99 | 0.191 | 18.17 | 100 | 100 |
| 1-13 | 18.12 | 0.183 | 18.17 | 100 | 100 |
| 1-14 | 18.35 | 0.190 | 18.17 | 100 | 100 |
| 1-15 | 15.31 | 0.125 | 15.69 | 100 | 100 |
| 2-1 | 15.86 | 0.129 | 15.69 | 100 | 100 |
| 2-2 | 15.16 | 0.122 | 15.69 | 100 | 100 |
| 2-3 | 15.10 | 0.121 | 15.69 | 100 | 100 |
| 2-4 | 15.13 | 0.121 | 15.69 | 100 | 100 |
| 2-5 | 15.69 | 0.127 | 15.69 | 100 | 100 |
| 2-6 | 16.13 | 0.173 | 15.69 | 100 | 100 |
| 2-7 | 15.45 | 0.128 | 15.69 | 100 | 100 |
| 2-8 | 15.32 | 0.125 | 15.69 | 100 | 100 |
| 2-9 | 15.39 | 0.125 | 15.69 | 100 | 100 |
| 2-10 | 16.02 | 0.171 | 15.69 | 100 | 100 |
| 2-11 | 18.51 | 0.215 | 18.17 | 100 | 100 |
| 2-12 | 18.30 | 0.189 | 18.17 | 100 | 100 |
| 2-13 | 18.39 | 0.187 | 18.17 | 100 | 100 |
| 2-14 | 18.45 | 0.201 | 18.17 | 100 | 100 |

As shown in the results of Tables 3 to 6, it can be seen that, when the formulation disclosed in WO 2007/149334 (i.e., Formulation 1-13) was stored under the accelerated condition (25° C.) and the stress condition (40° C.) for 8 weeks, the dimeric and multimeric impurities derived from aflibercept were formed in high levels. And also, in Formulations 1-14 and 2-13, which were prepared by using the same ionic tonicity agent and sugar as in the known formulation (i.e., Formulation 1-13) and adjusting the pH using the sodium acetate buffer as in Formulation 1-3, the dimeric and multimeric impurities derived from aflibercept were formed in similar levels to the known formulation (i.e., Formulation 1-13). From these results, it can be confirmed that the formation of dimeric and multimeric impurities derived from aflibercept is significantly increased by the ionic tonicity agent (for example, NaCl). In addition, it can be also confirmed that, in cases of the formulations (i.e., Formulations 2-11 and 2-12) containing the citrate salt buffering agent instead of the acetate salt buffering agent, the citrate functions as an ionic salt, thereby significantly increasing the formation of aflibercept-derived dimeric and multimeric impurities.

Ophthalmic formulations having various pHs which were prepared by increasing the amount of sugar without the use of the ionic tonicity agent (i.e., Formulations 1-1 to 1-12 and Formulations 2-1 to 2-10) were stored under the accelerated condition (25° C.) and the stress condition (40° C.) for 8 weeks and then the dimeric and multimeric impurities derived from aflibercept were measured. As the results thereof, the formulations which have pH 5.2 to 5.7 and are free of the ionic tonicity agent, i.e., Formulations 1-2, 1-3, 1-4, 1-8, 1-9, 1-10 and 2-1 to 2-10, showed significantly reduced formation of the dimeric and multimeric impurities derived from aflibercept. Especially, the formulations which have pH 5.5 and are free of the ionic tonicity agent, i.e., Formulations 1-3, 1-9, 2-2, 2-3, 2-4, 2-7, 2-8, and 2-9 showed remarkably reduced formation of the dimeric and multimeric impurities derived from aflibercept. In addition, Formulation 1-15 prepared using the same components as in Formulation 1-3 except for using sugar alcohol (sorbitol) instead of sugar also showed remarkably reduced formation of the dimeric and multimeric impurities derived from aflibercept. Among them, Formulations 1-15, 2-2, 2-3, 2-4, 2-7, 2-8, and 2-9 exhibited conventionally-acceptable effective osmolality range in an eye drop formulation, i.e., osmolality from about 230 to 320 mOsmol/kg. Especially, since Formulations 2-3 and 2-8 exhibited the osmolality ranging from about 270 to 310 mOsmol/kg, which is compatible with the osmolality of physiological saline (290 mOsmol/kg), it can be seen that said formulations are able to be very usefully used as ophthalmic formulations.

(3) Evaluation on the Formation of Fragments, Dimer, and Multimer Derived from Aflibercept Under the Cold Storage Condition (Under the 4° C. Condition)

After the storage of Formulations 2-1 to 2-10, 1-13, 2-13 and 2-14 in a 3 ml glass vial at 4° C. for 6 months and 12 months, the contents of aflibercept (monomer) and its fragments, dimers or multimers were measured according to the same methods as in the above (2). The SEC-HPLC analysis results are shown in Tables 7 and 8; and the DLS analysis results are shown in Tables 9 and 10.

TABLE 7

Results of SEC-HPLC Analysis (stored at 4° C. for 6 months)

| Formulation | Aflibercept (monomer) | Fragments | Dimers | Multimers |
|---|---|---|---|---|
| 2-1 | 98.7 | N.D* | 1.3 | N.D* |
| 2-2 | 98.8 | N.D* | 1.2 | N.D* |
| 2-3 | 99.1 | N.D* | 0.9 | N.D* |
| 2-4 | 98.9 | N.D* | 1.1 | N.D* |
| 2-5 | 98.6 | N.D* | 1.4 | N.D* |
| 2-6 | 98.4 | N.D* | 1.6 | N.D* |
| 2-7 | 98.7 | N.D* | 1.3 | N.D* |
| 2-8 | 98.9 | N.D* | 1.1 | N.D* |
| 2-9 | 98.9 | N.D* | 1.1 | N.D* |
| 2-10 | 98.6 | N.D* | 1.4 | N.D* |
| 1-13 | 98.1 | N.D* | 1.9 | N.D* |
| 2-13 | 97.9 | N.D* | 2.1 | N.D* |
| 2-14 | 97.8 | N.D* | 2.2 | N.D* |

*N.D.: not detected

TABLE 8

Results of SEC-HPLC Analysis (stored at 4° C. for 12 months)

| Formulation | Aflibercept (monomer) | Fragments | Dimers | Multimers |
|---|---|---|---|---|
| 2-1 | 98.1 | N.D* | 1.9 | N.D* |
| 2-2 | 98.5 | N.D* | 1.5 | N.D* |
| 2-3 | 98.7 | N.D* | 1.3 | N.D* |
| 2-4 | 98.6 | N.D* | 1.4 | N.D* |
| 2-5 | 98.4 | N.D* | 1.6 | N.D* |
| 2-6 | 98.0 | N.D* | 1.9 | 0.1 |
| 2-7 | 98.5 | N.D* | 1.5 | N.D* |
| 2-8 | 98.6 | N.D* | 1.4 | N.D* |
| 2-9 | 98.4 | N.D* | 1.6 | N.D* |
| 2-10 | 98.3 | N.D* | 1.7 | N.D* |
| 1-13 | 97.6 | N.D* | 2.3 | 0.1 |
| 2-13 | 97.4 | N.D* | 2.5 | 0.1 |
| 2-14 | 97.1 | N.D* | 2.7 | 0.2 |

*N.D.: not detected

TABLE 9

Results of DLS Analysis (stored at 4° C. for 6 months)

| Formulation | Z-Average (d · nm) | PDI | Peak Mean size (d · nm) | Intensity (100%) | Mass (100%) |
|---|---|---|---|---|---|
| 2-1 | 8.455 | 0.071 | 8.721 | 100 | 100 |
| 2-2 | 8.213 | 0.064 | 8.721 | 100 | 100 |
| 2-3 | 8.059 | 0.066 | 8.721 | 100 | 100 |
| 2-4 | 8.088 | 0.065 | 8.721 | 100 | 100 |
| 2-5 | 8.351 | 0.069 | 8.721 | 100 | 100 |
| 2-6 | 8.721 | 0.075 | 8.721 | 100 | 100 |
| 2-7 | 8.433 | 0.071 | 8.721 | 100 | 100 |
| 2-8 | 8.412 | 0.070 | 8.721 | 100 | 100 |
| 2-9 | 8.498 | 0.071 | 8.721 | 100 | 100 |
| 2-10 | 8.566 | 0.076 | 8.721 | 100 | 100 |
| 1-13 | 10.64 | 0.088 | 10.10 | 100 | 100 |
| 2-13 | 10.71 | 0.089 | 10.10 | 100 | 100 |
| 2-14 | 10.84 | 0.087 | 10.10 | 100 | 100 |

TABLE 10

Results of DLS Analysis (stored at 4° C. for 12 months)

| Formulation | Z-Average (d · nm) | PDI | Peak Mean size (d · nm) | Intensity (100%) | Mass (100%) |
|---|---|---|---|---|---|
| 2-1 | 9.246 | 0.085 | 10.10 | 100 | 100 |
| 2-2 | 8.964 | 0.077 | 10.10 | 100 | 100 |
| 2-3 | 8.709 | 0.074 | 8.721 | 100 | 100 |
| 2-4 | 8.725 | 0.075 | 8.721 | 100 | 100 |
| 2-5 | 9.192 | 0.082 | 10.10 | 100 | 100 |
| 2-6 | 9.526 | 0.087 | 10.10 | 100 | 100 |
| 2-7 | 9.167 | 0.080 | 10.10 | 100 | 100 |
| 2-8 | 8.918 | 0.078 | 10.10 | 100 | 100 |
| 2-9 | 8.920 | 0.077 | 10.10 | 100 | 100 |
| 2-10 | 9.389 | 0.088 | 10.10 | 100 | 100 |
| 1-13 | 12.35 | 0.098 | 13.54 | 100 | 100 |
| 2-13 | 12.59 | 0.102 | 13.54 | 100 | 100 |
| 2-14 | 12.62 | 0.101 | 13.54 | 100 | 100 |

As shown in the results of Tables 7 to 10, it can be seen that, when the formulations were stored at 4° C. for 6 months and 12 months, both the formulations free of the ionic tonicity agent (i.e., Formulations 2-1 to 2-10) and the formulations containing the ionic tonicity agent (i.e., Formulations 1-13, 2-13, and 2-14) showed the aflibercept-derived dimeric and multimeric impurities in low level. However, the formulations free of the ionic tonicity agent showed the aflibercept-derived dimeric and multimeric impurity formation in significantly lower levels, in comparison with the formulations containing the ionic tonicity agent.

(4) Analysis of Asparagine (Asn) Deamidation

Formulations 1-2, 1-3, 1-4, 1-8, 1-9, 1-10, 1-13, 1-14, 1-15, 2-1 to 2-10, 2-13 and 2-14, which were stored under the accelerated condition (25° C.) and the stress condition (40° C.) for 8 weeks in the above, were subjected to asparagine (Asn) deamidation analysis, i.e., isoaspartate quantitative analysis for the quantification of asparagine deamidation, thereby evaluating the protein modification therefrom. In addition, Formulations 2-1 to 2-10, 1-13, 2-13 and 2-14, which were stored under the 4° C. condition for 6 months and 12 months, were also subjected to isoaspartate quantitative analysis, thereby evaluating the protein modification therefrom.

The asparagine deamidation analysis was performed according to the manufacturer's instructions using the ISO- QUANT™ Isoaspartate Detection Kit (Promega, Cat. # MA1010). The results thereof are shown in Tables 11 to 14.

TABLE 11

Results of Asn Deamidation Analysis
(stored at 25° C. for 8 weeks)

| Formulation | Total Area | Deamidation product (Isoasp.) (pmol) |
|---|---|---|
| 1-2 | 41.80 | 16.4 |
| 1-3 | 34.50 | 13.6 |
| 1-4 | 37.30 | 14.7 |
| 1-8 | 43.40 | 17.1 |
| 1-9 | 39.10 | 15.4 |
| 1-10 | 45.20 | 17.8 |
| 1-13 | 58.20 | 22.9 |
| 1-14 | 57.60 | 22.6 |
| 1-15 | 40.80 | 16.0 |
| 2-1 | 40.90 | 16.1 |
| 2-2 | 35.20 | 13.8 |
| 2-3 | 34.70 | 13.4 |
| 2-4 | 34.90 | 13.4 |
| 2-5 | 37.50 | 14.9 |
| 2-6 | 43.70 | 17.3 |
| 2-7 | 39.80 | 15.8 |
| 2-8 | 38.60 | 15.2 |
| 2-9 | 38.80 | 15.3 |
| 2-10 | 46.10 | 18.5 |
| 2-13 | 59.30 | 23.2 |
| 2-14 | 60.30 | 24.6 |

TABLE 12

Results of Asn Deamidation Analysis
(stored at 40° C. for 8 weeks)

| Formulation | Total Area | Deamidation product (Isoasp.) (pmol) |
|---|---|---|
| 1-2 | 194.70 | 76.6 |
| 1-3 | 148.10 | 58.3 |
| 1-4 | 155.50 | 61.1 |
| 1-8 | 224.40 | 88.2 |
| 1-9 | 174.60 | 68.7 |
| 1-10 | 195.90 | 77.8 |
| 1-13 | 263.40 | 103.6 |
| 1-14 | 257.20 | 101.7 |
| 1-15 | 175.10 | 68.9 |
| 2-1 | 192.20 | 75.1 |
| 2-2 | 149.20 | 59.4 |
| 2-3 | 147.80 | 58.1 |
| 2-4 | 148.20 | 58.3 |
| 2-5 | 162.10 | 64.8 |
| 2-6 | 220.20 | 85.2 |
| 2-7 | 176.30 | 69.0 |
| 2-8 | 175.50 | 68.8 |
| 2-9 | 175.90 | 68.9 |
| 2-10 | 197.20 | 78.9 |
| 2-13 | 259.20 | 103.1 |
| 2-14 | 259.50 | 108.8 |

TABLE 13

Results of Asn Deamidation Analysis
(stored at 4° C. for 6 months)

| Formulation | Total Area | Deamidation product (Isoasp.) (pmol) |
|---|---|---|
| 2-1 | 9.6 | 3.9 |
| 2-2 | 9.4 | 3.7 |
| 2-3 | 9.3 | 3.6 |
| 2-4 | 9.4 | 3.6 |
| 2-5 | 9.7 | 3.8 |
| 2-6 | 9.7 | 4.0 |
| 2-7 | 9.5 | 3.7 |
| 2-8 | 9.5 | 3.8 |
| 2-9 | 9.4 | 3.7 |
| 2-10 | 9.8 | 4.0 |
| 1-13 | 10.8 | 4.8 |
| 2-13 | 10.5 | 4.6 |
| 2-14 | 10.7 | 5.1 |

TABLE 14

Results of Asn Deamidation Analysis
(stored at 4° C. for 12 months)

| Formulation | Total Area | Deamidation products (Isoasp.) (pmol) |
|---|---|---|
| 2-1 | 11.6 | 5.4 |
| 2-2 | 11.1 | 5.0 |
| 2-3 | 10.8 | 4.8 |
| 2-4 | 10.7 | 4.9 |
| 2-5 | 11.2 | 5.5 |
| 2-6 | 11.8 | 5.7 |
| 2-7 | 11.4 | 5.6 |
| 2-8 | 11.1 | 5.1 |
| 2-9 | 11.3 | 5.2 |
| 2-10 | 12.0 | 5.8 |
| 1-13 | 13.3 | 6.8 |
| 2-13 | 13.8 | 7.1 |
| 2-14 | 13.5 | 7.2 |

As shown in the results of Tables 11 to 14, it can be seen that the composition of the present invention, i.e., Formulations 1-2, 1-3, 1-4, 1-8, 1-9, 1-10 and 2-1 to 2-10, which were stored under the accelerated condition (25° C.) and the stress condition (40° C.) for 8 weeks, showed significantly reduced formation of the deamidation products. Especially, the formulations which have pH 5.5 and are free of the ionic tonicity agent, i.e., Formulations 1-3, 1-9, 2-3 and 2-9 showed remarkably reduced formation of the deamidation products.

And also, when Formulations 2-1 to 2-10, 1-13, 2-13 and 2-14 were stored at 4° C. for 6 months and 12 months, both the formulations free of the ionic tonicity agent (i.e., Formulations 2-1 to 2-10) and the formulations containing the ionic tonicity agent (i.e., Formulations 1-13, 2-13, and 2-14) showed the deamidation products in low level. However, the formulations free of the ionic tonicity agent showed the deamidation product formation in significantly lower levels, in comparison with the formulations containing the ionic tonicity agent.

(5) Evaluation on Inhibition Against Cell Proliferation

Biological activities were evaluated for Formulations 1-3, 1-13, 2-3, 2-8, and 2-13, which were stored under the accelerated condition (25° C.) for 8 weeks and under 4° C. for 12 months in the above. If human umbilical vein endothelial cells (HUVECs) are treated with vascular endothelial growth factor (VEGF), the cells are proliferated. Under said condition, the in vitro test was performed to evaluate the inhibition against the cell proliferation, according to the aflibercept treatment thereto.

The test was carried out at the final concentration of 50 ng/ml of rhVEGF$_{165}$ (Promokine, Cat. # C-64420) and at the concentration gradient from 2.4 to 2500 ng/ml of aflibercept.

Neutralization reaction was performed at 37° C. in a humidified 5% $CO_2$ incubator for 3 hours. The cells were treated with the reaction product and then cultured for 3 days. In order to evaluate the inhibition against cell proliferation, the absorbance at 590 nm was measured according to the CellTiter 96™ AQueous One Solution Cell Proliferation Assay (Promega, Cat. # G3580, MTS Solution) protocol, to determine the concentration required for half (50%) inhibition ($IC_{50}$).

The $IC_{50}$ values of each formulation obtained from the cell proliferation inhibition test as in the above are shown in Table 15.

TABLE 15

| | $IC_{50}$ (ng/ml) | |
| --- | --- | --- |
| | Stored at 25° C. for 8 weeks | Stored at 4° C. for 12 months |
| Formulation 1-3 | 119.30 | 118.24 |
| Formulation 1-13 | 144.54 | 122.96 |
| Formulation 2-3 | 118.27 | 117.50 |
| Formulation 2-8 | 119.52 | 119.63 |
| Formulation 2-13 | 146.42 | 124.55 |

As shown in the results of Table 15, it can be seen that, when stored under the accelerated condition for a long time, the ophthalmic formulations obtained according to the present invention not only have excellent stability but also exhibit the biological activities increased by about 20 to 25% in comparison with the conventional formulation. In addition, it can be also seen that, when stored under the 4° C. storage condition, the formulations free of the ionic tonicity agent have superior biological activity to the formulation containing the ionic tonicity agent.

(6) Evaluation on Inhibition Against Tube Formation

Tube formation assay of human umbilical vein endothelial cells (HUVECs) was performed for Formulations 1-3, 1-13, 2-3, 2-8, and 2-13, which were stored under the accelerated condition (25° C.) for 8 weeks in the above. Human umbilical vein endothelial cells (HUVECs) form tubes in a Matrigel-coated plate. The treatment of HUVECs with vascular endothelial growth factor (VEGF) increases the tube formation ability of HUVECs. Under said condition, the in vitro test was performed to evaluate the inhibition against the tube formation ability, according to the aflibercept treatment thereto.

10 µl of Matrigel (BD Matrigel, Growth Factor Reduced, Cat. #356231) was into each well of the Ibidi's µ-Slide Angiogenesis, ibiTreat (Cat. #81506) kit and then polymerization reaction was performed at 37° C. for 2 hours. The final concentration of $rhVEGF_{165}$ (Promokine, Cat. # C-64420) was set to 1.56 nM (about 60 ng/ml) and aflibercept was set to have a concentration of 10 nM (about 1150 ng/ml). Incubation was performed at 37° C. in a humidified 5% $CO_2$ incubator for 3 hours. The cells ($1\times10^4$ cells/50 µl) were mixed with the incubation product and then added into each µ-Slide Angiogenesis well coated with Matrigel. After about 16 hours therefrom, the tube formation was observed.

The tube formation of HUVECs was photographed with a microscope and then the degree of tube formation was evaluated using the Angiogenesis analyzer for Image J program distributed by the National Institutes of Health (NIH). The inhibition of tube formation was evaluated by measuring the number of tubes and the number of branching points forming the tubes.

The results of each formulation obtained from the inhibition test against tube formation of HUVECs as in the above are shown in Table 16 and FIG. 1.

TABLE 16

Evaluations of inhibition against tube formation of HUVECs (stored at 25° C. for 8 weeks)

| | Number of Tubes (3 well average) | S.D | Number of Branching points (3 well average) | S.D |
| --- | --- | --- | --- | --- |
| Control | 16 | 2.52 | 68 | 8.09 |
| VEGF (1.56 nM) | 33 | 2.51 | 103 | 2.18 |
| VEGF (1.56 nM) + Formulation 1-3 (10 nM) | 15 | 4.16 | 69 | 4.26 |
| VEGF (1.56 nM) + Formulation 1-13 (10 nM) | 24 | 3.05 | 81 | 5.13 |
| VEGF (1.56 nM) + Formulation 2-3 (10 nM) | 14 | 2.08 | 63 | 5.69 |
| VEGF (1.56 nM) + Formulation 2-8 (10 nM) | 16 | 2.23 | 66 | 4.93 |
| VEGF (1.56 nM) + Formulation 2-13 (10 nM) | 26 | 4.12 | 84 | 6.51 |

And also, the same tests as in the above were carried out for the formulations stored at 4° C. for 12 months. The results thereof are shown in Table 17.

TABLE 17

Evaluations of inhibition against tube formation of HUVECs (storage at 4° C. for 12 months)

| | Number of Tubes (3 well average) | S.D | Number of Branching points (3 well average) | S.D |
| --- | --- | --- | --- | --- |
| Control | 17 | 2.89 | 70 | 7.02 |
| VEGF (1.56 nM) | 35 | 2.08 | 106 | 3.79 |
| VEGF (1.56 nM) + Formulation 1-3 (10 nM) | 16 | 0.58 | 64 | 6.03 |
| VEGF (1.56 nM) + Formulation 1-13 (10 nM) | 18 | 1.53 | 66 | 4.16 |
| VEGF (1.56 nM) + Formulation 2-3 (10 nM) | 15 | 1.15 | 63 | 4.00 |
| VEGF (1.56 nM) + Formulation 2-8 (10 nM) | 17 | 2.00 | 64 | 6.43 |
| VEGF (1.56 nM) + Formulation 2-13 (10 nM) | 21 | 1.53 | 73 | 2.65 |

As shown in the results of Table 16 and the FIGURE, it can be seen that, when stored under the accelerated condition for a long time, the ophthalmic formulations obtained according to the present invention not only have excellent stability compared to the conventional formulation but also exhibit a similar level of tube forming ability to that of the control group, i.e., exhibit remarkably increased inhibition of tube formation in comparison with the formulation containing the ionic tonicity agent. In addition, it can be also seen that, when stored under the 4° C. storage condition, the formulations free of the ionic tonicity agent have superior inhibitory activity against the tube formation of HUVECs to the formulation containing the ionic tonicity agent.

The invention claimed is:

1. An ophthalmic pharmaceutical composition having a pH ranging from pH 5.2 to 5.7, comprising (a) a therapeutically effective amount of aflibercept; (b) 10 to 20 mM of a sodium acetate buffering agent; (c) 6 to 8 w/v % of a sugar or 3 to 7 w/v % of a sugar alcohol; and (d) 0.01 to 0.1 w/v % of a surfactant in an aqueous medium, wherein the ophthalmic pharmaceutical composition is free of an ionic tonicity agent.

2. The ophthalmic pharmaceutical composition according to claim 1, wherein the aflibercept is present in a concentration ranging from 20 to 50 mg/ml.

3. The ophthalmic pharmaceutical composition according to claim 1, wherein the sugar is sucrose, trehalose, or a mixture thereof.

4. The ophthalmic pharmaceutical composition according to claim 1, wherein the sugar is sucrose.

5. The ophthalmic pharmaceutical composition according to claim 1, wherein the sugar alcohol is sorbitol.

6. The ophthalmic pharmaceutical composition according to claim 5, wherein the sorbitol is present in a concentration of about 5 w/v %.

7. The ophthalmic pharmaceutical composition according to claim 1, wherein the surfactant is polyoxyethylene sorbitan fatty acid ester, polyoxyethylene-polyoxypropylene block copolymer, or a mixture thereof.

8. The ophthalmic pharmaceutical composition according to claim 7, wherein the surfactant is polyoxyethylene (20) sorbitan monolaurate or polyoxyethylene (20) sorbitan monooleate.

9. The ophthalmic pharmaceutical composition according to claim 8, wherein the surfactant is polyoxyethylene (20) sorbitan monolaurate.

10. The ophthalmic pharmaceutical composition according to claim 9, wherein the surfactant is present in a concentration of about 0.03 w/v %.

11. An ophthalmic pharmaceutical composition having a pH of about 5.5, consisting of 40 mg/ml of aflibercept; 10 to 15 mM of a sodium acetate buffering agent; 7 w/v % of sucrose; 0.03 w/v % of polyoxyethylene (20) sorbitan monolaurate, and an aqueous medium.

12. An ophthalmic pharmaceutical composition having a pH of about 5.5, consisting of 40 mg/ml of aflibercept; 10 to 15 mM of a sodium acetate buffering agent; 8 w/v % of trehalose; 0.03 w/v % of polyoxyethylene (20) sorbitan monolaurate, and an aqueous medium.

* * * * *